(12) United States Patent
Shim et al.

(10) Patent No.: US 8,431,623 B2
(45) Date of Patent: Apr. 30, 2013

(54) PROCESS FOR FORMING A POROUS PVA SCAFFOLD USING A PORE-FORMING AGENT

(75) Inventors: Young-Bock Shim, Seoul (KR); Hong-Hee Jung, Seoul (KR); Yon-Rak Choi, Suwon-si (KR); Ju-Woong Jang, Seoul (KR)

(73) Assignee: Korea Bone Bank Co., Ltd., Seoul (KR)

( * ) Notice: Subject to any disclaimer, the term of this patent is extended or adjusted under 35 U.S.C. 154(b) by 0 days.

(21) Appl. No.: 13/383,647

(22) PCT Filed: May 10, 2010

(86) PCT No.: PCT/KR2010/002951
§ 371 (c)(1),
(2), (4) Date: Jan. 12, 2012

(87) PCT Pub. No.: WO2011/007952
PCT Pub. Date: Jan. 20, 2011

(65) Prior Publication Data
US 2012/0108689 A1     May 3, 2012

(30) Foreign Application Priority Data
Jul. 13, 2009   (KR) .......................... 10-2009-0063695

(51) Int. Cl.
*C08J 9/08*     (2006.01)
*B29C 35/18*     (2006.01)

(52) U.S. Cl.
USPC ................. 521/141; 521/56; 521/92; 521/97; 524/425

(58) Field of Classification Search .......................... None
See application file for complete search history.

(56) References Cited

U.S. PATENT DOCUMENTS 6,268,405 B1 * 7/2001 Yao et al. ...................... 523/113
2009/0305024 A1 * 12/2009 Gvozdic .................... 428/304.4

FOREIGN PATENT DOCUMENTS

| JP | 63-276488 | * 11/1988 |
| KR | 10-2003-0065795 | 8/2003 |
| KR | 10-2003-0097691 | 12/2003 |
| KR | 10-0429000 | 4/2004 |
| KR | 10-2008-0033335 | 4/2008 |
| KR | 10-2008-0034031 | 4/2008 |

OTHER PUBLICATIONS abstract for "Rheological and Foaming Behaviors of Plasticized Poly(vinyl alcohol)" authored by Wu et al. and published in Zhongguo Suliao (2011) 25(8), 69-74.*

* cited by examiner

*Primary Examiner* — Marc Zimmer
(74) *Attorney, Agent, or Firm* — Valauskas Corder LLC

(57) ABSTRACT

The present invention relates to a process for forming a porous poly(vinyl alcohol) (PVA) scaffold using a pore-forming agent, comprising: mixing PVA with the pore-forming agent to form micropores in the PVA scaffold and using an easily decomposable pore-forming agent after the formation of the pores to improve convenience and reduce the processing time in manufacturing the porous PVA scaffold as well as to enable a pore size and porosity to be selected. A process for forming a porous PVA scaffold using a pore-forming agent according to the present invention includes heating to melt the PVA, cooling the melted PVA and mixing the PVA with a heat-decomposable pore-forming agent, repeating the freezing/thawing of the mixed PVA to cure the PVA mixture, and stirring the cured PVA mixture with a hydrochloric acid solution at a high temperature of 65° C. or more to produce foam.

8 Claims, 4 Drawing Sheets

PROCESS FOR FORMING A POROUS PVA SCAFFOLD USING A PORE-FORMING AGENT

RELATED APPLICATION DATA

This application claims priority from PCT/KR2010/002951, filed May 10, 2010, which claims priority from Korean Application No. KR 10-2009-0063695 filed Jul. 13, 2009.

TECHNICAL FIELD

The present invention relates to a process for forming a porous polyvinyl alcohol scaffold using polyvinyl alcohol - termed "PVA" for purposes of this application - and a pore-forming agent, and more particularly, to a process for forming a porous PVA scaffold using a pore-forming agent, comprising: mixing PVA with the pore-forming agent to form micropores in the PVA scaffold and using a pore-forming agent easily decomposable during the formation of pores, thereby providing enhanced convenience and reducing the processing time in manufacturing the porous PVA scaffold and also allowing control of the pore size and porosity of the scaffolds.

BACKGROUND ART

Recently, there have been attempts to restore damaged tissues through in vitro production of a part of said tissues, and various studies have been done in the field of tissue engineering. Tissue engineering is an application science which involves understanding the structure-function relationship in tissues based on the principles of life science and biotechnology and further developing biological substitutes for transplant into the human bodies to maintain, enhance or restore the functions of the human bodies. As it is recognized that there is a need for development of artificial organs or regeneration of tissues by using tissue engineering, many studies have been done on the techniques for attaching desired cells to different natural or synthetic polymer materials and implanting the cell-polymer composite in the body to reproduce tissues or organs.

The ideal polymer scaffold is a so-called porous scaffold that consists of a nontoxic material having biocompatibility for not causing blood coagulation or inflammation after implantation. In addition, this scaffold has excellent mechanical properties to support the growth of cells. For purposes of this application, the term "mechanical" may be defined as "structural". Moreover, in its form, this scaffold permits good adhesion of cells as well as sufficient space between cells to allow cells to access oxygen or nutrients through diffusion of body fluid and to form new blood vessels actively, which results in successful cell growth and differentiation. Furthermore, cells are generally cultured on a two-dimensional surface, but a three-dimensional scaffold is required to culture cells to become tissues or organs. These three-dimensional scaffolds are preferable to permit a number of pores that may adhere cells and also include an open structure for supplying nutrients necessary for cell growth and secreting waste products from the cells.

Since the polyvinyl alcohol (PVA) scaffolds are non-toxic with good biocompatibility and can be easily prepared, they are used in wound dressing, contact lenses, and drug delivery systems, and many studies have been done in which scaffolds are used for biomaterials based on their strong mechanical and physical properties. In particular, the PVA scaffold contains a number of micropores capable of taking up a large amount of water, while exhibiting low substance-permeability. Therefore, under a weight load, the PVA scaffold causes the gel to excrete a liquid, which acts as a lubricant in the space between the bones, and the PVA scaffold has a surface structure similar to that of real cartilage and high water content. Accordingly, the PVA scaffold is particularly suitable as an artificial transplant material of cartilage.

As disclosed above, the PVA scaffold can be useful as a polymer scaffold material such as artificial cartilage material in the tissue engineering field. Therefore, it is required to have a sufficient mechanical strength to maintain its structure during normal usage as a scaffold, and to easily form a porous structure to help in regenerating tissues.

Much research has been done on the methods for ensuring the mechanical strength of the PVA scaffold, and thus a method has been established to provide the strength by physically or chemically crosslinking PVA. While the chemical method may cause toxicity in vivo due to a chemical crosslinking agent or an initiator, the physical crosslinking method is preferred to impart an appropriate strength to the PVA scaffold without adverse effects such as toxicity. The representative examples include a radiation method, a freeze/thaw method, or the like.

Meanwhile, the conventional method for providing porosity in the PVA scaffold includes the solvent-casting and particle-leaching technique which comprises mixing water-soluble polymers, sugars, salts, etc. to form a scaffold, and then dissolving these solutes in water to form pores. However, the water-soluble polymer can produce pores, but often forms a hydrogen bond with the OH-group of PVA to change the properties of the PVA. Sugars or salts such as NaCl temporarily increase the viscosity of PVA in the preparation of PVA scaffolds, making the preparation process almost impossible. Moreover, all of these substances are difficult to remove after formation of pores, and the removal becomes more difficult when the pores remain deep inside the PVA scaffolds. Due to difficulty in removing the remaining pore-forming agent, the time required to remove the pore-forming agent after crosslinking is at least 5 days, causing inefficiency in the preparation work. In addition, these pore-forming agents only form pores in the PVA scaffolds, but do not permit control of the pore size and the porosity within a specific range.

DISCLOSURE

Technical Problem

The present invention is intended to solve the above-mentioned problems occurring in the prior art. Specifically, it is an object of the present invention to provide a method for preparing porous PVA scaffolds using a pore-forming agent to form pores in the PVA scaffolds, in which the pore-forming agent does not cause an increase in the viscosity of the PVA solution when mixed with PVA, thus allowing easiness in preparation of the scaffolds; it can be easily removed during formation of pores due to degradability by heat or an acid solution, contributing to improved convenience and reduction of the processing time; and it can be adjusted in its particle size or proportion, resulting in the control of pore size and porosity in the PVA scaffolds.

Technical Solution

To achieve the object of the present invention, there is a method for preparing a porous PVA scaffold using a pore-forming agent, comprising: melting PVA by heat; cooling the melted PVA and mixing the PVA with a thermodegradable pore-forming agent; repeatedly freezing/thawing the PVA mixed with the pore-forming agent to cure the PVA mixture; and stirring the cured PVA mixture with a hydrochloric acid solution at 65 to 100° C. to form pores.

In one preferred embodiment, the PVA is heated with a solvent at 100° C. for 50 minutes.

In one preferred embodiment, the thermodegradable pore-forming agent is sodium hydrogen carbonate ($NaHCO_3$), ammonium hydrogen carbonate ($NH_4HCO_3$), or a mixture of these.

In one preferred embodiment, the content of the PVA is from 5 to 40% by weight.

In one preferred embodiment, the PVA and the pore-forming agent are mixed at a ratio of 1:1 to 1:15.

ADVANTAGEOUS EFFECTS

The method for preparing a porous PVA scaffold using a pore-forming agent according to the present invention uses a pore-forming agent such as a material capable of forming uniform porous scaffolds without increasing viscosity when mixed with PVA and capable of being easily removable by heat or an acid solution. Accordingly, it reduces the time required to remove the pore-forming agent after PVA crosslinking to about one to two days, which is shorter than the time usually required in the prior art, i.e., at least 5 days. In addition, the viscosity of said pore-forming agent does not increase even after it is mixed with PVA, and thus the PVA scaffold can be easily prepared. Furthermore, the pore size and porosity of the porous PVA scaffold can be controlled by adjusting the particle size and the proportion of the pore-forming agent.

MODE FOR INVENTION

The embodiments of the present invention will be explained in detail with reference to the attached drawings.

Figure 1:
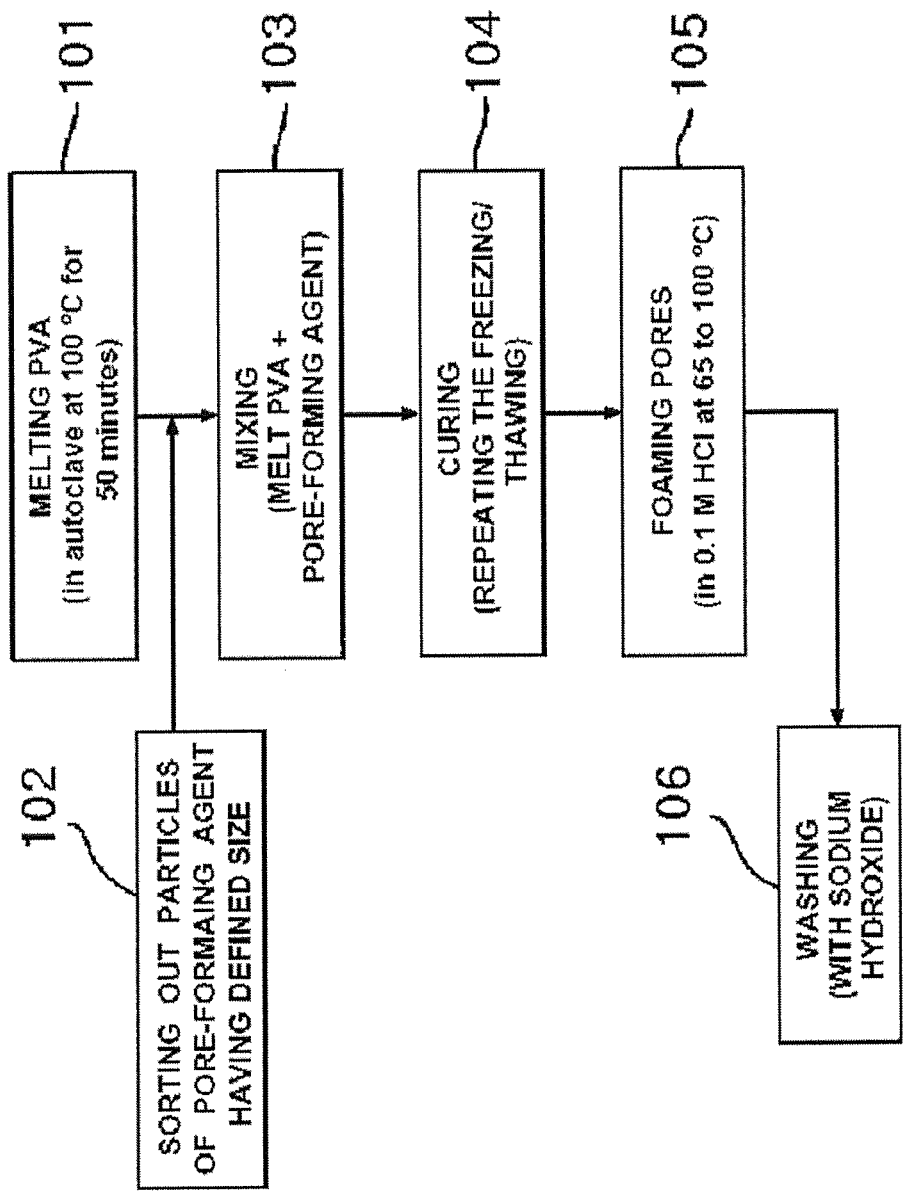
FIG. 1 is a flow chart showing a method for preparing a porous PVA scaffold using a pore-forming agent.

FIG. 1 is a flow chart showing a method for preparing a porous PVA scaffold using the pore-forming agent of the present invention.

Referring to FIG. 1, the first step (101) of the method according to the present invention is melting PVA. The raw material, polyvinyl alcohol (PVA) is put in a container, and then heated at 100° C. for 50 minutes in a heating apparatus to melt the PVA until there is no solid PVA left (in step 101). In this step, the concentration of the PVA used as a raw material is from 5 to 40% by weight. If the PVA content is less than 5% by weight, it causes poor mechanical properties of the final porous PVA scaffold, while if the PVA content is more than 40% by weight, it causes an excessive rise of the viscosity, causing a problem in the process, such as difficulty stirring.

The subsequent optional step (102) is selecting the particle size of the pore-forming agent. The particles of the pore-forming agent are sorted out within the range of 100 to 500 μm by using a microsieve (in step 102). The use of the particles within said defined size range may allow formation of pores having a uniform size. In other words, the pore size and the porosity in the product can be controlled by adjusting the particle size of the pore-forming agent and the mixing ratio of PVA to the pore-forming agent as described below. In one preferred embodiment, the porous PVA scaffold prepared has an average pore size of 50 to 650 μm and a porosity of 80%.

The pore-forming agent used in the method of the present invention is a thermodegradable pore-forming agent that is degradable by heat or a hydrochloric solution, preferably sodium hydrogen carbonate ($NaHCO_3$), ammonium hydrogen carbonate ($NH_4HCO_3$), or a mixture of these, which are typically used for antacids, medicinal products, baking powders, etc. These materials produce pores during degradation by heat or a hydrochloric acid. In this embodiment, degradation is not achieved by treatment of chemicals, but by heating. Therefore, various advantages are provided in the preparing process. Moreover, sugar, NaCl, KCl, etc. used in the prior art cause difficulty in the process by increasing the viscosity of PVA due to physical and chemical bonds when mixed with PVA, whereas sodium hydrogen carbonate ($NaHCO_3$) and ammonium hydrogen carbonate ($NH_4HCO_3$) used as a pore-forming agent in the present invention do not raise the viscosity of PVA when mixed with PVA, allowing easier production of porous PVA scaffolds.

The next step (103) is mixing PVA and the pore-forming agent together. The melted PVA is cooled down to about 60° C., and then mixed with the pore-forming agent at a ratio of 1:1 to 1:15 (PVA to the pore-forming agent), in step (103). The mixing ratios less than 1:1 results in a failure in formation of pores to a desired extent, while the mixing ratio greater than 1:15 causes the pore-forming agent to inhibit the inter-PVA crosslinking, causing difficulty in formation of porous PVA scaffolds. Control of the mixing ratio of PVA to the pore-forming agent allows control of the number of pores or the porosity in the porous PVA scaffolds produced. In other words, the porosity may rise with an increase in the proportion of the pore-forming agent in the mixture. In the aspect of pore size and water content of the porous PVA scaffolds, the mixing ratio of PVA to the pore-forming agent is preferably from 1:5 to 1:10. The mixing ratio of PVA to the pore-forming agent is more preferably in the range of 1:8 to 1:10, in which case the resultant porous PVA scaffolds have pores connected to one another. Different mixing techniques may be used, although the use of a paste mixer is preferred. The use of said paste mixer allows preparing a uniform mixture of PVA and the pore-forming agent and simultaneously removing pores, and also enhances the mechanical strength of the final product by stirring the mixture vigorously even when PVA having high-concentration and high-viscosity is used. A centrifugal machine, which is operated to eliminate pores rather than to mix PVA and the pore-forming agent together, may be used in the process in which stirring and pore elimination are separately carried out, even though it does not have a paste mixer. In other words, the centrifugal equipment can be used at least for removing pores from PVA.

The next step (104) is curing the PVA. The curing of PVA is conducted through a freeze/thaw method in order to form physical cross-linkage of PVA. Especially, when ammonium hydrogen carbonate is used as a pore-forming agent, it is preferable to first perform an instantaneous freezing process at −70° C. for one hour in order to minimize degradation of ammonium hydrogen carbonate. Although the freeze/thaw method may be carried out in various manners, the number of freeze/thaw repetitions is preferably determined to acquire a desired strength, because the repetition of the freeze/thaw process is intended to enhance the strength through crosslinking. It is evident that the number of freeze/thaw repetitions depends on the PVA content, the content of the pore-forming agent, and the particle size, which are factors affecting the strength of the porous PVA scaffolds. For example, with 5 to 40% by weight of PVA, sufficient curing can be achieved after five repetitions of 6-hour freezing at −20° C. or below and 4-hour thawing at room temperature.

The cross-linked PVA scaffold, provided with structural strength, can be molded. For example, a biopsy punch having 5 mm of diameter may be used for molding cylindrical shapes of a same size in large quantities. The conventional molding method, which includes injecting hydrogel into a pre-made mold to yield a single product from a single mold, has a problem in the large-scale production of scaffolds. However, the method of the present invention includes injection into molds and thus allows a large-scale production of scaffolds with high strength in a single press molding process.

The next step (105) is foaming the PVA. The cured mixture of PVA and the pore-forming agent is put in a hydrochloric acid solution at a high temperature to produce a foam. As thermodegradation occurs at 65° C. or above for sodium hydrogen carbonate and at 60° C. or above for ammonium hydrogen carbonate, it is preferable to put the mixture of PVA and pore-forming agent into a 0.1 N hydrochloric acid solution at 65 to 100° C. and then stir. In this embodiment, the required stirring time is two days for sodium hydrogen carbonate and one day for ammonium hydrogen carbonate. Such a stirring process causes thermodegradation of the pore-forming agent to produce pores in the PVA scaffolds. Therefore, there is no need for a separate process for removing the pore-forming agent in the present invention, since the pore-forming agent forms pores through thermodegradation and is removed at the same time. Meanwhile, the use of a hydrochloric acid solution, which is an acid solution suitable for degradation of the pore-forming agent of the present invention such as sodium hydrogen carbonate and ammonium hydrogen carbonate, allows the pore-forming agent to produce pores rapidly without increasing the temperature of degradation and to be removed at once. As mentioned above, sodium hydrogen carbonate, for example, takes 1 to 2 days for complete degradation at high speed, while the conventional pore-forming agents such as polymers, sugars and salts typically take 5 or more days. Furthermore, sodium hydrogen carbonate produces sodium carbonate, vapor and $CO_2$ as by-products of degradation. All of these are nontoxic to the human body, and thus do not lower the biocompatibility of the porous PVA scaffolds.

The subsequent optional step (106) is washing out the PVA scaffolds. The PVA scaffold degraded by the hydrochloric acid solution exhibits acidity, which can be eliminated by neutralization with a base solution such as sodium hydroxide or by washed with a sufficient amount of distilled water, thereby completing a porous PVA scaffold (in step 106).

EXAMPLE 1

Figure 2:
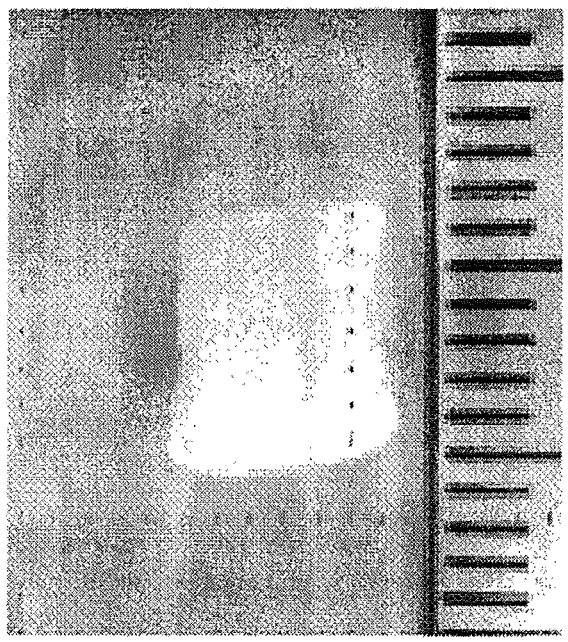
FIG. 2 presents pictures showing porous PVA scaffolds prepared according to one embodiment of the present invention.
Figure 2:
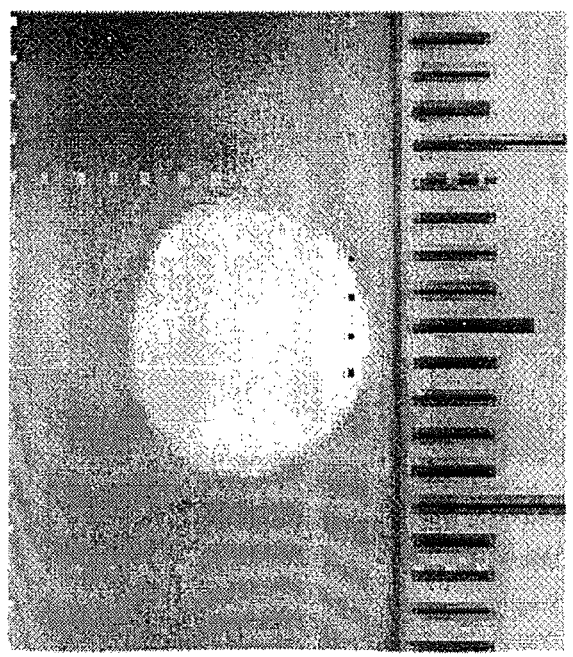
Figure 3:
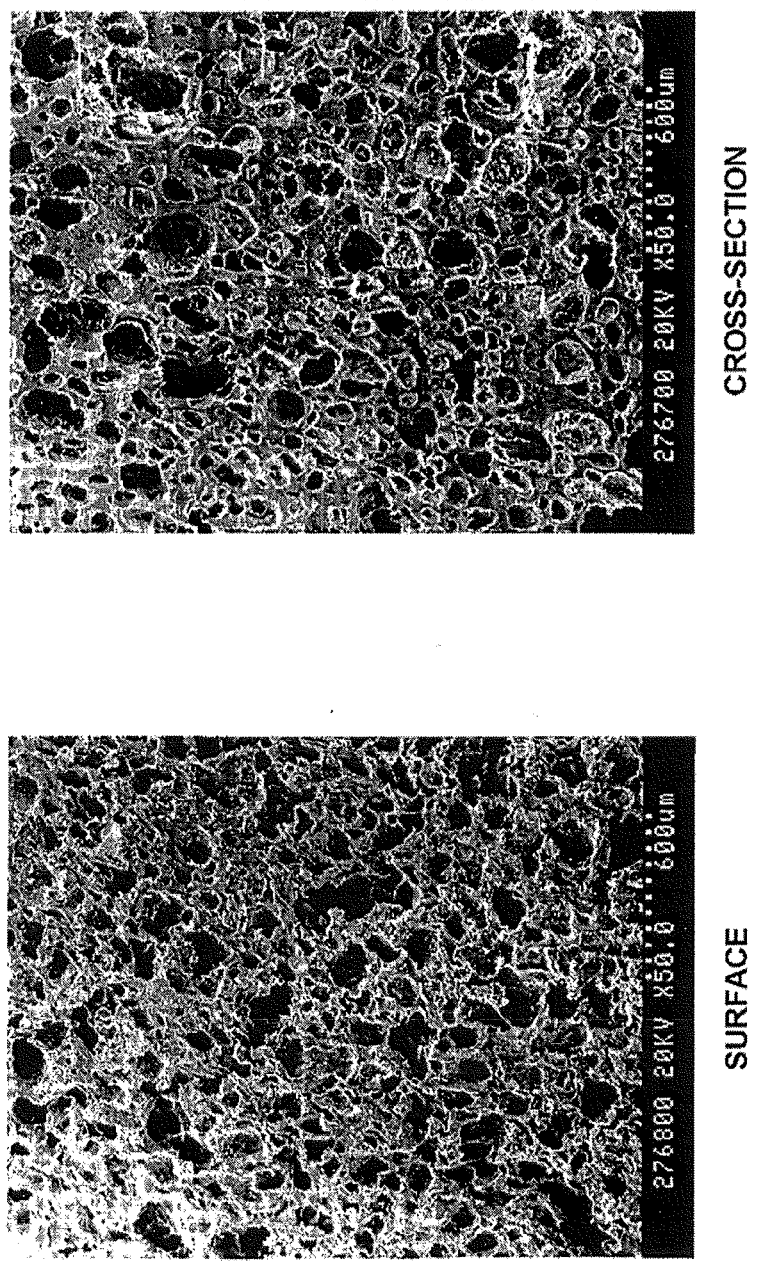
FIG. 3 presents SEM pictures showing the surface and the cross-section of a porous PVA scaffold prepared according to one embodiment of the present invention.

3 g of PVA (average molecular weight: 146,000 to 186,000) was added to 15 ml of water to prepare 20% by weight of PVA solution, and then put in heating equipment and melted at 100° C. for 50 minutes. The completely melted PVA was cooled down to 60° C. and then mixed with 24 g of sodium hydrogen carbonate having 200μm of size. A PVA scaffold was prepared by five repetitions of 6-hour freezing at −20° C. and 2-hour thawing at room temperature. A 5mm-diameter punch was used to prepare 5×10 mm cylindrical scaffolds. The PVA scaffold thus obtained was put in 500 ml of 0.1 N HCl solution at 70° C., and then stirred for 48 hours to remove sodium hydrogen carbonate and produce pores, whereby the porous PVA scaffold of the present invention was prepared. The resultant porous PVA scaffold in the form of cylinder is illustrated in FIG. 2, and its surface and cross-section are shown in the SEM pictures of FIG. 3. As seen in FIG. 3, the PVA scaffold has uniform pores connected to one another. For purposes of this application, the term "SEM" means "scanning electron microscope".

EXAMPLE 2

Figure 4:
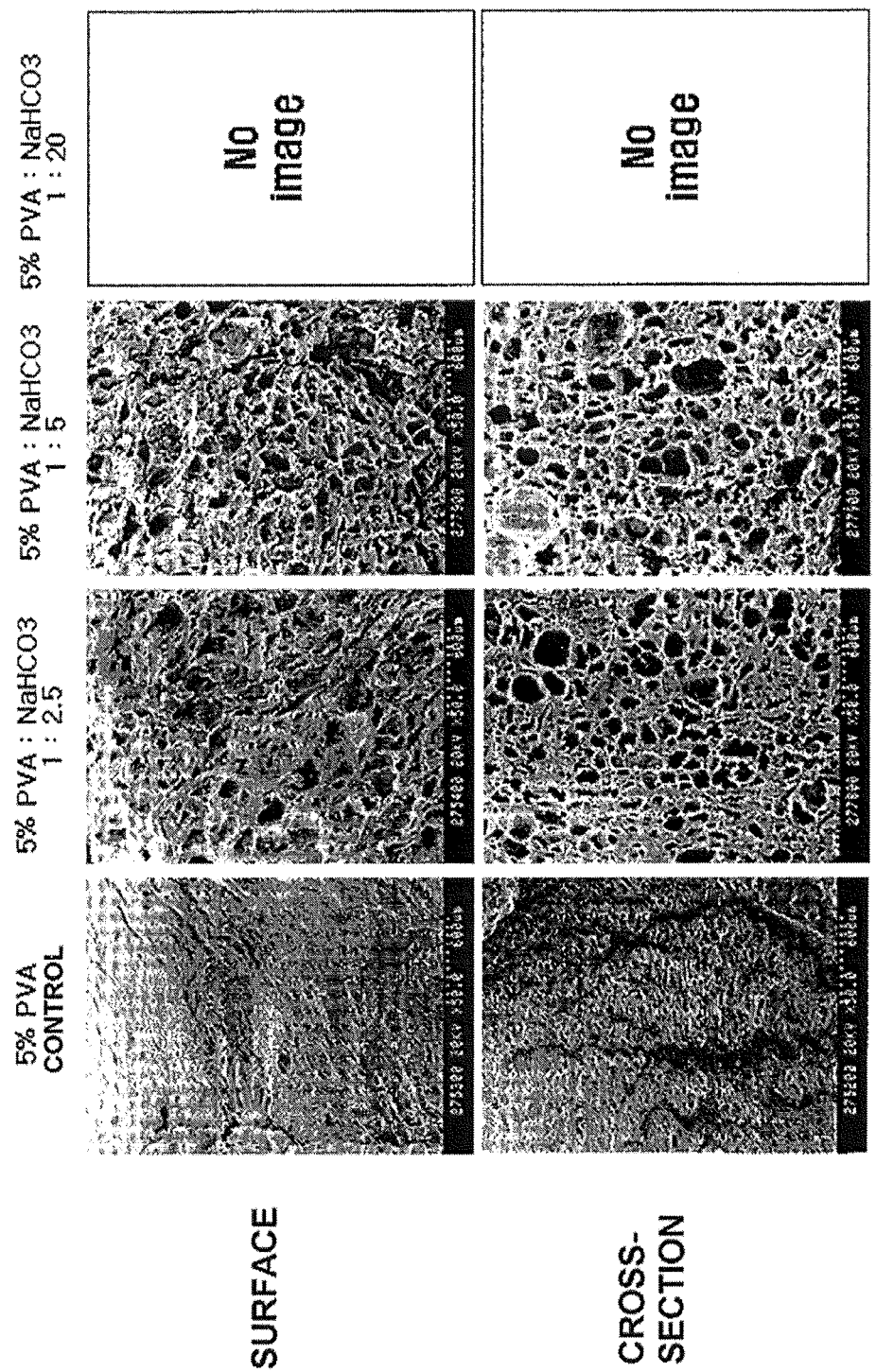
FIG. 4 presents SEM pictures showing the porous PVA scaffolds prepared by using 5% PVA and varying proportions of the pore-forming agent.

The procedure was conducted in the same manner as described in Example 1 to prepare porous PVA scaffolds, excepting that the PVA concentration was 5%, with the mixing ratios of PVA to sodium hydrogen carbonate 1:1, 1:2.5, 1:5, and 1:20. The SEM pictures of the porous PVA scaffolds are presented in FIG. 4, and the water content thereof was measured. As seen in FIG. 4, the porosity increased with an increase in the proportion of the pore-forming agent in the mixture, and PVA scaffold was not prepared when the mixing ratio of PVA to sodium hydrogen carbonate was 1:20. All of the porous PVA scaffolds prepared had a high water content of 95% or more.

EXAMPLE 3

The procedure was conducted in the same manner as described in Example 1 to prepare a porous PVA scaffold, excepting that 24 g of ammonium hydrogen carbonate was used instead of sodium hydrogen carbonate and that stirring was carried out for one day.

In the above, although the invention has been described with preferred embodiments, it is to be understood that variations and modifications may be made to as will be apparent to those skilled in the art without changing the technical ideas and essential features.

What is claimed is:

1. A method for preparing a porous PVA scaffold using PVA and a pore-forming agent, comprising:
    melting the PVA by heat;
    cooling down the PVA and mixing the PVA with the pore-forming agent to form a PVA mixture;
    repeatedly freezing/thawing the PVA mixture to form a cured PVA mixture; and
    stirring the cured PVA mixture with a hydrochloric acid solution at a temperature of 65 to 100° C. to form the porous PVA scaffold.

2. The method as claimed in claim 1, wherein the PVA has a concentration of 5 to 40% by weight.

3. The method as claimed in claim 1, wherein the pore-forming agent is at least one selected from the group consisting of sodium hydrogen carbonate ($NaHCO_3$), ammonium hydrogen carbonate ($NH_4HCO_3$), and a mixture thereof.

4. The method as claimed in claim 1, wherein the PVA mixture includes the PVA and the pore-forming agent in a ratio of 1:1 to 1:15.

5. The method as claimed in claim 1, further comprising:
    subsequent to melting the PVA by heat, using a microsieve to sort particles of the pore-forming agent into various particle sizes and retaining the particles having a defined range of particle size.

6. The method as claimed in claim 5, wherein the defined range of particle size of the pore-forming agent is 100 to 300 µm.

7. The method as claimed in claim 1, wherein a centrifugal machine is used to eliminate pores from the PVA while mixing the PVA with the pore-forming agent.

8. The method as claimed in claim 1, further comprising:
   subsequent to stirring the cured PVA mixture with the hydrochloric acid solution at a temperature of 65 to 100° C. to form the porous PVA scaffold, washing out the porous PVA scaffold with a base solution or distilled water.

\* \* \* \* \*